United States Patent [19]

Siegel et al.

[11] 4,146,649

[45] Mar. 27, 1979

[54] SKIN MOISTURIZING COMPOSITION CONTAINING A POLYETHOXY FATTY ALCOHOL AND A POLYETHOXY GLYCOSIDE

[75] Inventors: Maurice L. Siegel, Hillsdale; Melvin F. Weiss, Pine Brook, both of N.J.

[73] Assignee: Faberge, Incorporated, New York, N.Y.

[21] Appl. No.: 732,461

[22] Filed: Oct. 14, 1976

[51] Int. Cl.$^2$ ............................................. A61K 7/48
[52] U.S. Cl. .................................... 424/361; 424/319; 424/365
[58] Field of Search .................. 424/361, 319, 365; 536/4, 120

[56] References Cited

U.S. PATENT DOCUMENTS

| | | | |
|---|---|---|---|
| 2,407,001 | 9/1946 | Griffin | 536/120 |
| 2,759,922 | 8/1956 | Gibbons | 260/210 |
| 2,759,923 | 8/1956 | Gibbons | 260/210 |
| 2,945,024 | 7/1960 | De Groote et al. | 536/120 |
| 3,042,666 | 7/1962 | Gentles | 536/120 |
| 3,085,085 | 4/1963 | Wismer et al. | 536/120 X |
| 3,098,795 | 7/1963 | Kreps | 424/365 |
| 3,231,472 | 1/1966 | Jacob et al. | 424/365 |
| 3,300,474 | 1/1967 | Flodin et al. | 424/361 X |
| 3,422,204 | 1/1969 | Edman | 424/361 |
| 3,471,624 | 10/1969 | Youngblood | 424/362 |
| 3,535,427 | 10/1970 | Miller et al. | 424/365 |
| 3,659,025 | 4/1972 | Halleck | 424/361 |
| 3,689,678 | 9/1972 | Fox et al. | 424/365 |
| 3,734,902 | 5/1973 | McNaughton et al. | 260/210 R |
| 3,835,169 | 9/1974 | Kraft et al. | 424/365 X |
| 3,846,556 | 11/1974 | Handjani et al. | 424/364 |
| 3,896,238 | 7/1975 | Smith | 424/358 |
| 3,934,003 | 1/1976 | Fuma et al. | 424/361 X |
| 3,957,969 | 5/1976 | Fujiyama et al. | 424/361 X |
| 4,011,389 | 3/1977 | Langdon | 536/4 |

FOREIGN PATENT DOCUMENTS

| | | | |
|---|---|---|---|
| 37-18096 | 11/1962 | Japan | 424/365 |
| 47-3330 | 1/1972 | Japan | 424/365 |
| 368267 | 5/1963 | Switzerland | 424/361 |

*Primary Examiner*—Albert T. Meyers
*Assistant Examiner*—Vera C. Clarke
*Attorney, Agent, or Firm*—Davis, Hoxie, Faithfull & Hapgood

[57] ABSTRACT

This invention relates to a skin moisturizing composition composed of polyethoxylated fatty alcohol, polyethoxylated glycoside, water and minor quantities of water soluble salt and amino acid or urea, which composition both penetrates the skin surface and retains moisture near the skin surface.

7 Claims, No Drawings

SKIN MOISTURIZING COMPOSITION CONTAINING A POLYETHOXY FATTY ALCOHOL AND A POLYETHOXY GLYCOSIDE

This invention relates to a skin moisturizing composition formed of generally water soluble components of which the main components are emulsifying and hydrophyllic in character, tending to penetrate the skin and carry with it hydrophyllic components, and more particularly, the skin moisturizer herein is composed of higher ethoxylated fatty alcohols and glycosides with minor quantities of hydrophyllic substances which, in combination with the emulsifying components, readily penetrate the skin surface and retain moisture near the surface to impart to the skin surface a softened, moisturized and non-oily character.

The main emulsifying component of the skin moisturizer is an ethoxylated higher fatty alcohol having from 12 - 20 carbon atoms of saturated or unsaturated aliphatic chain, preferably alcohols derived from lanolin, and ethoxylated with a sufficient number of polyethoxy groups, 6 to 30 and usually 10 to 12, to convert the fatty alcohol to water soluble form. The ethoxylated fatty alcohol component is a main emulsifying component and is usually used in quantity ranging 30 to 60% by weight of the composition, and preferably about 45 to 55%.

A second penetrating component of this moisturizing composition is a polyethoxy glycoside, typically glucose or higher natural sugars or polyhydric alcohols having 6 to 15, typically 8 - 12, ethoxy groups. The polyethoxy glycoside has an emulsifying and skin penetrating function as well as a moisture attractive function both as a skin penetrant and moisture concentrating agent as used in the present composition. For this purpose it will be used in concentration of about 15 to 35% by weight and preferably from about 20 to 30%.

A third major component is water, preferably distilled or deionized at least to softened form. When the composition is used as a concentrate for further dilution by aqueous solution additions, the initial water component may be in the range of 10 to 20% by weight of the concentrate, and in the diluted form, the water component will range from 17 to 40%.

A further component of the composition is a water soluble salt, typically a non-irritating salt of an alkali or alkaline earth metal such as sodium, potassium, magnesium or calcium with an anion, typically a chloride, monobasic phosphate, acetate, citrate, formate or lactate. The salt is usually used in minor quantity of a few percent down to even trace quantities, such as from about 0.01 up to about 5% by weight, and preferably between about 3 and 4%. The water soluble salt performs a moisture attractive function both as a skin penetrant and moisture concentrating agent.

A further component of the moistening composition hereof is urea or an amino acid having 2 to 6 carbon atoms, typically L-proline, L-histidine, glycine and the like. The amino acid component may vary in quantity from about 0.01 up to 5% by weight of composition, and preferably is used in a quantity ranging from 0.05 to 5% of the composition. The amino acid performs a moisture attractive function both as a skin penetrant and moisture concentrating agent.

The composition is formed by merely mixing the components together to form a homogeneous solution.

As thus described, the composition comprises ethoxylated higher alcohols having an ethoxy content sufficient to solubilize the same, ethoxylated glycosides, the ethoxy and hydroxyl content of which has a high emulsifying effect, and water with smaller contents of water soluble salts and lower amino acids and urea. The composition is skin penetrative and water soluble, and has a moisture concentrating effect. All of the components have a skin softening effect and, being skin penetrating, provide a smooth skin moistening and softening effect, entering the skin without leaving a greasy film.

The following examples are typical:

EXAMPLE I

| | Weight Percent |
|---|---|
| Ethoxylated lanolin alcohol having 16 ethoxy groups per lanolin alcohol molecule | 49 |
| Ethoxylated glucose having 10 ethoxy groups per glucose molecule | 25 |
| Water | 18.67 |
| Salt | 3.98 |
| Amino acid having 1 - 6 carbon atoms | 3.35 |

EXAMPLE II

The formulation of Example I is reproduced substituting sodium chloride for the salt, deionized water for the water component, and L-proline for the amino acid.

EXAMPLE III

Example I was repeated substituting distilled water for the water, magnesium chloride for the salt, and L-histidine for the amino acid.

EXAMPLE IV

Example I was repeated substituting a mixture of urea and glycine for the amino acid, and sodium lactate for the salt.

EXAMPLE V

Example I was repeated substituting L-proline for the amino acid and a mixture of equal parts of magnesium chloride, basic sodium phosphate and potassium citrate for the salt.

EXAMPLE VI

Several formulations and tests were made, tests 1, 2, 3 and 4 having the compositions and results as listed in the following table. The table compares results in absorption tests applied to leather strips as a moisturizer study, the strips immersed for 24-hour periods and dried alternately in separate tests at 45° C. showing by weight gain percentages the amount of moisture absorbed.

| PRODUCT | NUMBER | FIRST WEIGHING | LAST WEIGHING | DIFFERENCE | WEIGHT GAIN % |
|---|---|---|---|---|---|
| Example 1 | 1 | 0.2206 | 0.3491 | 0.1285 | 58.25 |
| | | | 0.3396 | 0.1190 | 53.94 |
| | | | 0.3552 | 0.1273 | 55.86 |
| Example 1 | 2 | 0.2279 | 0.3324 | 0.1045 | 45.85 |
| | | | 0.3471 | 0.1225 | 54.54 |

-continued

| PRODUCT | NUMBER | FIRST WEIGHING | LAST WEIGHING | DIFFERENCE | WEIGHT GAIN % |
|---|---|---|---|---|---|
| Example 1 | 3 | 0.2246 | 0.3300 | 0.1054 | 46.93 |
|  |  |  | 0.3382 | 0.1353 | 66.68 |
| Example 1 | 4 | 0.2029 | 0.3299 | 0.1270 | 62.59 |
| Water 18.01% |  |  |  |  |  |
| Solulan 16 49.00% |  |  |  |  |  |
| Glucam E-20 25.00% |  |  | 0.3488 | 0.1140 | 48.55 |
| NaCl 3.98% | 5 | 0.2348 | 0.3372 | 0.1024 | 43.61 |
| Solulan 16 49.00% |  |  |  |  |  |
| Glucam E-20 25.00% |  |  | 0.3622 | 0.1454 | 67.07 |
| Water 18.67% | 6 | 0.2168 | 0.3529 | 0.1361 | 62.78 |
| NaCl 3.98% |  |  |  |  |  |
| L-proline 3.35% |  |  |  |  |  |
| Solulan 16 49.00% |  |  |  |  |  |
| Glucam E-20 25.00% |  |  |  |  |  |
| NaCl 3.98% |  |  | 0.3531 | 0.1161 | 48.99 |
| Water 18.67% | 7 | 0.2370 | 0.3451 | 0.1081 | 45.61 |
| L-proline 3.35% |  |  |  |  |  |
| Solulan 16 49.00% |  |  |  |  |  |
| Glucam E-20 25.00% |  |  |  |  |  |
| Water 18.67% |  |  | 0.3107 | 0.1242 | 66.60 |
| NaCl 3.98% | 8 | 0.1865 | 0.3076 | 0.1211 | 64.93 |
| L-proline 3.35% |  |  |  |  |  |
| Solulan 16 49.00% |  |  |  |  |  |
| Glucam E-20 25.00% |  |  | 0.3368 | 0.1139 | 51.10 |
| NaCl 3.98% | 9 | 0.2229 | 0.3232 | 0.1003 | 45.00 |
| Water 18.67% |  |  |  |  |  |
| L-histidine 3.35 |  |  |  |  |  |
| Solulan 16 48.00% |  |  |  |  |  |
| Glucam E-20 25.00% |  |  | 0.4685 | 0.1152 | 45.48 |
| NaCl 3.98% | 10 | 0.2533 | 0.3416 | 0.0883 | 34.86 |
| L-histidine 3.35% |  |  |  |  |  |
| Water 18.67% |  |  |  |  |  |
| Solulan 16 49.00% |  |  |  |  |  |
| Glucam E-20 25.00% |  |  | 0.3267 | 0.1076 | 49.11 |
| NaCl 3.98% | 11 | 0.2191 | 0.3145 | 0.0954 | 43.54 |
| Water 18.67% |  |  |  |  |  |
| Glycine 3.35% |  |  |  |  |  |
| Water 18.67% |  |  |  |  |  |
| Solulan 16 49.00% |  |  |  |  |  |
| Glucam E-20 25.00% |  |  | 0.2822 | 0.1006 | 55.40 |
| NaCl 3.98% | 12 | 0.1816 | 0.2738 | 0.0922 | 50.77 |
| Glycine 3.35% |  |  |  |  |  |
|  |  |  | 0.3529 | 0.01354 | 62.65 |
| Example 1 | 13 | 0.2175 | 0.3401 | 0.1226 | 56.37 |
|  |  |  | 0.3668 | 0.1511 | 70.05 |
| Example 1 | 14 | 0.2157 | 0.3521 | 0.1264 | 63.24 |

It is clear from the several tests applied to leather strips that the skin moisturizer hereof is substantially absorbable into the surface of a film similarly porous, leather being used for test purposes, and particularly that the several formulations are, in fact, absorbable into the leather in varying quantities and retained therein without imparting a greasy film.

The composition hereof may contain other additives to improve its attractiveness, such as perfuming agents and may be slightly tinted only sufficient to improve its sales attractiveness and the odorizer may be such as approved by F&DA.

What is claimed is:

1. A skin moisturizing composition comprising an ethoxylated higher fatty alcohol having from 12 to 20 carbon atoms, and from 6 to 30 ethoxy groups per molecule of higher alcohol in a quantity of 30 to 60%, a polyethoxy glycoside having from 6 to 15 ethoxy groups per sugar radical in a quantity of 15 to 35%, water in a quantity of 10 to 40%, a water soluble salt of an alkali or an alkaline earth metal having an anion selected from the group consisting of chloride, phosphate, citrate, formate, acetate and lactate in a quantity of 0.01 to 5%, and a compound selected from the group consisting of urea and an amino acid having 2 - 6 carbon atoms in a quantity of 0.01 to 5%, the proportions being by weight.

2. The skin moisturizer as defined in claim 1 wherein the ethoxylated higher fatty alcohol is present in a quantity of 45 to 55%, the polyethoxy glycoside is present in a quantity of 20 to 30%, the water is present in a quantity of 10 to 20%, the salt is present in a quantity of 3 to 4%, and the compound selected from the group consisting of urea and an amino acid is present in a quantity of 0.05 to 4%, the proportions being by weight.

3. The composition as defined in claim 1 wherein the ethoxylated higher fatty alcohol is an ether of lanolin alcohols having about 16 ethoxy groups per alcohol molecule.

4. The composition as defined in claim 1 wherein the polyethoxy glycoside is polyethoxy glucoside having about 10 ethoxy groups.

5. The composition as defined in claim 1 wherein the salt is selected from the group consisting of sodium lactate, calcium chloride, magnesium chloride, monobasic sodium phosphate, potassium citrate and sodium formate.

6. The skin moisturizer as defined in claim 1 wherein the amino acid is selected from the group consisting of L-proline, glycine, L-histidine, and mixtures thereof.

7. A skin moisturizer comprising an ethoxylated higher fatty alcohol having about 16 ethoxy groups in quantity ranging from 30 to 60%, ethoxylated glucose having about 10 ethoxy groups in a quantity ranging from 15 to 35%, water in a quantity ranging from 10 to 40%, a water soluble salt of an alkali or an alkaline earth metal having an anion selected from the group consisting of chloride, phosphate, citrate, formate, acetate and lactate in a quantity of 0.01 to 5%, and a compound selected from the group consisting of lower amino acids having 2 to 6 carbon atoms and urea in a quantity ranging from about 0.05 to 5%, the proportions being by weight.

* * * * *

UNITED STATES PATENT OFFICE
CERTIFICATE OF CORRECTION

PATENT NO. : 4,146,649
DATED : March 27, 1979
INVENTOR(S) : MAURICE L. SIEGEL and MELVIN F. WEISS It is certified that error appears in the above-identified patent and that said Letters Patent are hereby corrected as shown below:

Column 3, below the product "NaCl" on line 7 in the table, the following product and per cent should be inserted--L-proline 3.35%--.

Signed and Sealed this

Fifth Day of February 1980

[SEAL]

Attest:

SIDNEY A. DIAMOND

Attesting Officer  Commissioner of Patents and Trademarks